United States Patent
Braden et al.

(10) Patent No.: US 9,250,162 B2
(45) Date of Patent: Feb. 2, 2016

(54) DIRECT IMPACT AEROSOL SAMPLING BY ELECTROSTATIC PRECIPITATION

(71) Applicant: UT-Battelle, LLC, Oak Ridge, TN (US)

(72) Inventors: Jason D. Braden, Clinton, TN (US); Andrew G. Harter, Knoxville, TN (US); Brad J. Stinson, Knoxville, TN (US); Nicholas M. Sullivan, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 197 days.

(21) Appl. No.: 13/963,331

(22) Filed: Aug. 9, 2013

(65) Prior Publication Data

US 2015/0040760 A1 Feb. 12, 2015

(51) Int. Cl.
*G01N 1/22* (2006.01)
*B03C 3/82* (2006.01)
*B03C 3/47* (2006.01)
*B03C 3/09* (2006.01)
*B03C 3/12* (2006.01)
*B03C 3/32* (2006.01)
*B03C 3/41* (2006.01)
(Continued)

(52) U.S. Cl.
CPC .............. *G01N 1/2208* (2013.01); *B03C 3/09* (2013.01); *B03C 3/12* (2013.01); *B03C 3/32* (2013.01); *B03C 3/41* (2013.01); *B03C 3/47* (2013.01); *B03C 3/82* (2013.01); *G01N 1/2202* (2013.01); *G01N 15/0266* (2013.01); *G01N 2001/2223* (2013.01); *G01N 2015/0046* (2013.01)

(58) Field of Classification Search
CPC combination set(s) only.
See application file for complete search history.

(56) References Cited

U.S. PATENT DOCUMENTS 6,524,369 B1  2/2003  Krigmont
6,828,794 B2 * 12/2004  Reavell et al. ............... 324/464
(Continued)

FOREIGN PATENT DOCUMENTS

KR  1020080098567 A  11/2008
WO  WO 2007011400 A2 *  1/2007
(Continued)

OTHER PUBLICATIONS

Miller, A. et al., "A Handheld Electrostatic Precipitator for Sampling Airborne Particles and Nanoparticles" Aerosol Science and Technology (Apr. 20, 2010) pp. 417-427, vol. 44.
(Continued)

*Primary Examiner* — Duane Smith
*Assistant Examiner* — Sonji Turner
(74) *Attorney, Agent, or Firm* — Scully, Scott, Murphhy & Presser, P.C.

(57) ABSTRACT

The present disclosure provides apparatuses for collecting aerosol samples by ionizing an air sample at different degrees. An air flow is generated through a cavity in which at least one corona wire is disposed and electrically charged to form a corona therearound. At least one grounded sample collection plate is provided downstream of the at least one corona wire so that aerosol ions generated within the corona are deposited on the at least one grounded sample collection plate. A plurality of aerosol samples ionized to different degrees can be generated. The at least one corona wire may be perpendicular to the direction of the flow, or may be parallel to the direction of the flow. The apparatus can include a serial connection of a plurality of stages such that each stage is capable of generating at least one aerosol sample, and the air flow passes through the plurality of stages serially.

19 Claims, 13 Drawing Sheets

(51) Int. Cl.
*G01N 15/02* (2006.01)
*G01N 15/00* (2006.01)

(56) References Cited

U.S. PATENT DOCUMENTS

| | | | |
|---|---|---|---|
| 6,955,075 B2* | 10/2005 | Carlson et al. | 73/28.02 |
| 7,077,890 B2 | 7/2006 | Botvinnik | |
| 7,160,391 B2* | 1/2007 | Willey et al. | 118/629 |
| 7,404,847 B2 | 7/2008 | Hess | |
| 7,428,848 B2* | 9/2008 | Pant et al. | 73/863.21 |
| 7,641,718 B2 | 1/2010 | Furuta et al. | |
| 8,167,986 B2* | 5/2012 | Schneider et al. | 96/61 |
| 8,398,746 B2* | 3/2013 | Black et al. | 95/78 |
| 2004/0080321 A1* | 4/2004 | Reavell et al. | 324/458 |
| 2004/0083790 A1* | 5/2004 | Carlson et al. | 73/28.02 |
| 2007/0234901 A1* | 10/2007 | Pletcher et al. | 95/78 |
| 2010/0075317 A1* | 3/2010 | Schneider et al. | 435/6 |
| 2011/0185904 A1 | 8/2011 | Langle et al. | |
| 2011/0315011 A1* | 12/2011 | Black et al. | 95/79 |
| 2013/0032031 A1* | 2/2013 | Bartko et al. | 96/18 |

FOREIGN PATENT DOCUMENTS

| | | |
|---|---|---|
| WO | 2009035483 A2 | 3/2009 |
| WO | 2011133516 A1 | 10/2011 |

OTHER PUBLICATIONS

Zukeran, A. et al., "Two-Stage-Type Electrostatic Precipitator Re-Entrainment Phenomena Under Diesel Flue Gases" IEEE Transactions on Industry Applications (Mar./Apr. 1999) pp. 346-351, vol. 35, No. 2.

* cited by examiner

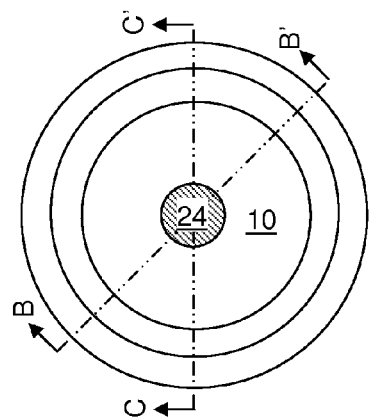
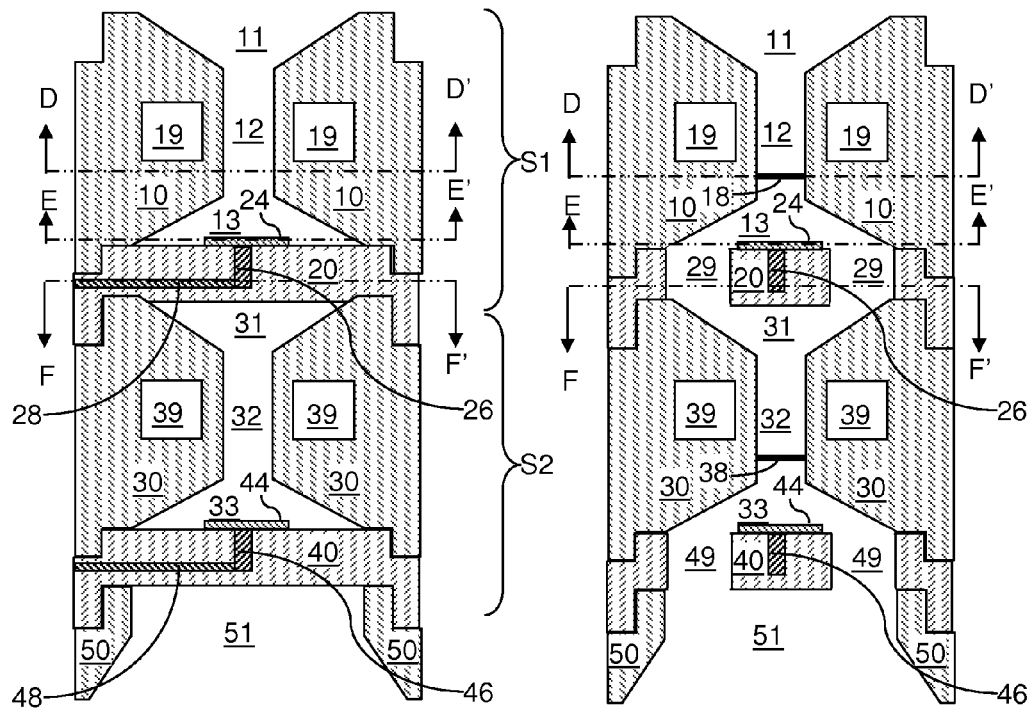
FIG. 1A
FIG. 1B FIG. 1C

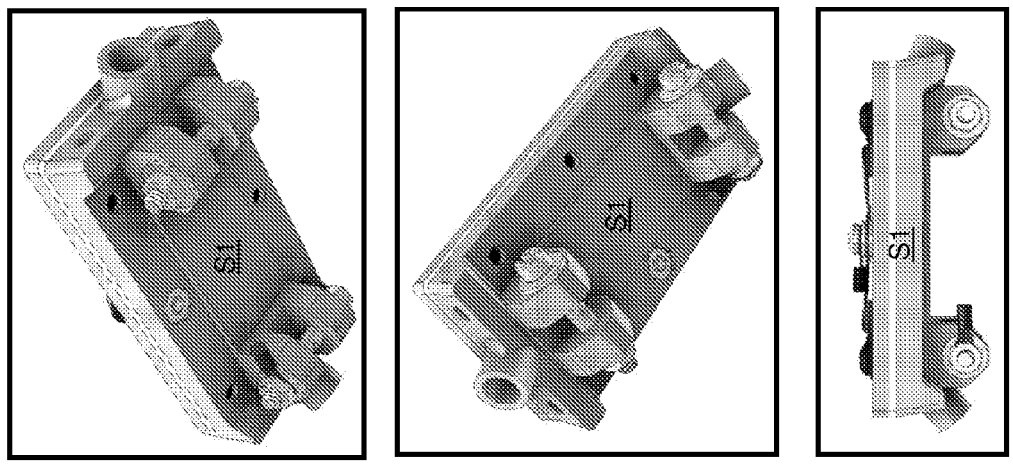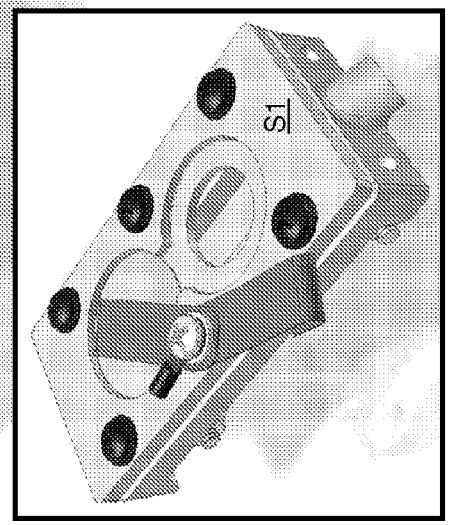
FIG. 6

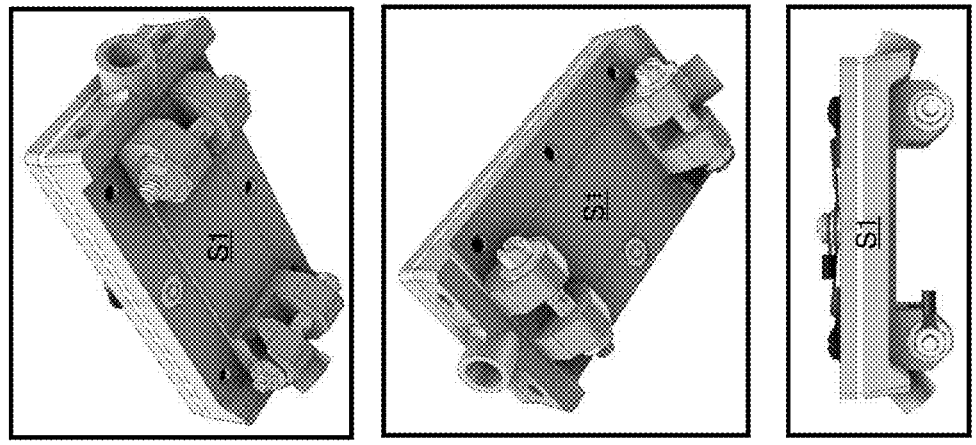
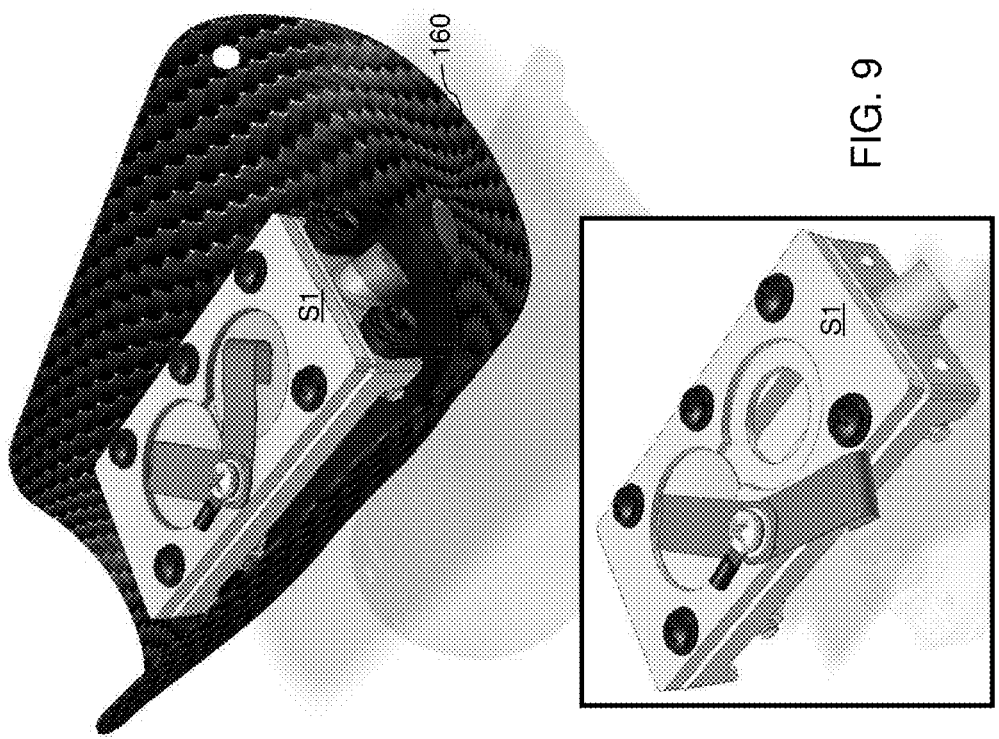
FIG. 9

DIRECT IMPACT AEROSOL SAMPLING BY ELECTROSTATIC PRECIPITATION

STATEMENT REGARDING FEDERALLY SPONSORED RESEARCH OR DEVELOPMENT

This invention was made with government support under Contract No. DE-AC05-00OR22725 awarded by the U.S. Department of Energy. The government has certain rights in this invention.

FIELD OF THE INVENTION

The present invention relates to aerosol sampling, and particularly to apparatus for sampling aerosols by electrostatic precipitation and methods of operating the same.

BACKGROUND OF THE INVENTION

Collection and analysis of aerosol samples can be an important step in measuring and diagnosing the composition and condition of air in various situations. Such collection and analysis of aerosol samples can be performed as a routine practice for monitoring purposes, or can be performed as an emergency task to assess environmental impact at a disaster site such as a chemical leakage site or a nuclear material leakage site. Thus, a systematic and efficient method for collecting aerosol samples from air at any arbitrary location is desirable.

SUMMARY OF THE INVENTION

The present disclosure provides apparatuses for collecting aerosol samples by ionizing an air sample at different degrees. An air flow is generated through a cavity in which at least one corona wire is disposed and electrically charged to form a corona therearound. At least one grounded sample collection plate is provided downstream of the at least one corona wire so that aerosol ions generated within the corona are deposited on the at least one grounded sample collection plate. A plurality of aerosol samples ionized to different degrees can be generated. The at least one corona wire may be perpendicular to the direction of the flow, or may be parallel to the direction of the flow. The apparatus can include a serial connection of a plurality of stages such that each stage is capable of generating at least one aerosol sample, and the air flow passes through the plurality of stages serially.

According to an aspect of the present disclosure, an electrostatic aerosol sampling apparatus is provided. A chamber of the electrostatic aerosol sampling apparatus includes a cavity therein. The cavity is connected to an air inlet channel and an air outlet channel, and is configured to allow an air flow therethrough. The electrostatic aerosol sampling apparatus further includes at least one corona wire located within the cavity, at least one grounded sample collection plate disposed downstream of a portion of the at least one corona wire, a high voltage application circuitry configured to generate a corona between the at least one corona wire and the at least one grounded sample collection plate, and at least one means for inducing an air flow into the air inlet channel through the cavity and out of the air outlet channel.

According to another aspect of the present disclosure, a method of collecting at least one aerosol sample is provided. A chamber of the electrostatic aerosol sampling apparatus includes a cavity therein. The cavity is connected to an air inlet channel and an air outlet channel, and is configured to allow an air flow therethrough. The electrostatic aerosol sampling apparatus further includes at least one corona wire located within the cavity, at least one grounded sample collection plate disposed downstream of a portion of the at least one corona wire, a high voltage application circuitry configured to generate a corona between the at least one corona wire and the at least one grounded sample collection plate, and at least one means for inducing an air flow into the air inlet channel through the cavity and out of the air outlet channel. Accumulation of an aerosol material on the at least one grounded sample collection plate is induced by causing air to pass through the cavity employing the at least one means for inducing the air flow while a corona is present between the at least one corona wire and each of the at least one grounded sample collection plate.

BRIEF DESCRIPTION OF THE DRAWINGS

FIG. 1A is a top-down view of a first exemplary electrostatic aerosol sampling apparatus according to a first embodiment of the present disclosure.

FIG. 1B is a cross-sectional view of the first exemplary electrostatic aerosol sampling apparatus along the plane B-B' of FIGS. 1A, 1D, 1E, and 1E.

FIG. 1C is a cross-sectional view of the first exemplary electrostatic aerosol sampling apparatus along the plane C-C' in FIGS. 1A, 1D, 1E, and 1E.

FIG. 6 shows various views of the sample of the second exemplary electrostatic aerosol sampling apparatus according to the second embodiment of the present disclosure.

DETAILED DESCRIPTION OF THE INVENTION

Figure 1D:
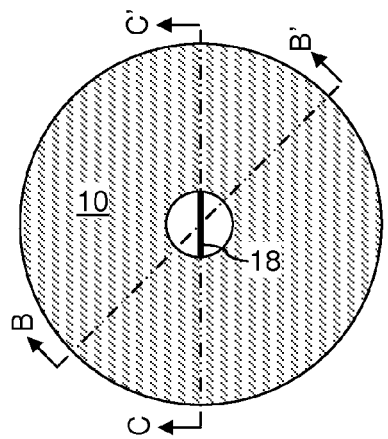
FIG. 1D is a cross-sectional view of the first exemplary electrostatic aerosol sampling apparatus along the plane D-D' in FIGS. 1B and 1C.
Figure 1E:
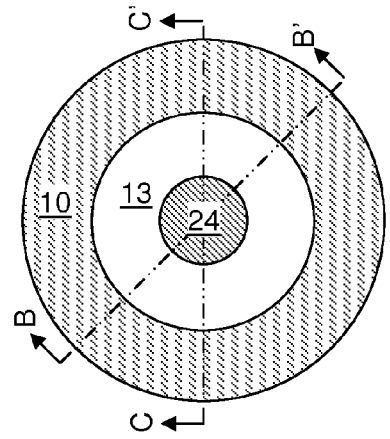
FIG. 1E is a cross-sectional view of the first exemplary electrostatic aerosol sampling apparatus along the plane E-E' in FIGS. 1B and 1C.
Figure 1F:
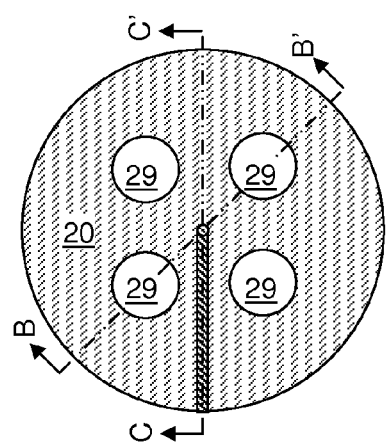
FIG. 1F is a cross-sectional view of the first exemplary electrostatic aerosol sampling apparatus along the plane F-F' in FIGS. 1B and 1C.

As stated above, the present invention relates apparatus for sampling aerosols by electrostatic precipitation and methods of operating the same. Aspects of the present disclosure are now described in detail with accompanying figures. Like and corresponding elements are referred to by like reference numerals. Proportions of various elements in the accompanying figures are not drawn to scale to enable clear illustration of elements having smaller dimensions relative to other elements having larger dimensions. As used herein, "a," "one," "another," "even another," "yet another," "still another," or other grammatical determiners are employed to distinguish one element from another element. As such, an element identified by a particular grammatical determiner in claims may, or may not, correspond to an element in the specification that employs the same grammatical determiner. As used herein, "first," "second," "third," and other ordinals are employed to distinguish one element from another element. As such, an element identified by a particular ordinal in claims may, or may not, correspond to an element in the specification that employs the same ordinal.

Referring to FIGS. 1A-1F, a first exemplary electrostatic aerosol sampling apparatus according to a first embodiment of the present disclosure is illustrated. The first exemplary electrostatic aerosol sampling apparatus includes a first stage S1 and a second stage S2 that are adjoined to each other such that air flow exiting the first stage S1 enters the second stage S2.

The first stage S1 includes a first cavity (11, 12, 13), which is configured to allow an air flow therethrough. In one embodiment, the first cavity (11, 12, 13) can include a first narrowing-taper conical cavity portion 11, a first cylindrical cavity portion 12 adjoining a narrow periphery of the narrowing-taper conical cavity portion 11, and a first widening-taper conical cavity portion 13 adjoining the first cylindrical cavity portion 12 at one end of the first cylindrical cavity portion 12.

As used herein, a "conical cavity portion" refers to a portion of a cavity substantially bounded by a side surface of a truncated cone. As used herein, a "side surface" of a truncated cone refers to the surface of the truncated cone other than a top surface and a bottom surface of the truncated cone. As used herein, a cavity is "substantially bounded by" a particular surface if more than 95% of the surfaces defining the cavity and the particular surface coincide. As used herein, a "narrowing-taper" conical cavity portion is a conical cavity portion in which the cross-sectional area of the conical cavity portion decreases along a reference direction. The reference direction in the first exemplary electrostatic aerosol sampling apparatus is the direction along which an air flow proceeds within the first cylindrical cavity portion 12. As used herein, a "widening-taper" conical cavity portion is a conical cavity portion in which the cross-sectional area of the conical cavity portion increases along the reference direction. As used herein, a first element adjoins a second element is an edge of the first element is the same as an edge of the second element.

Interior surfaces of a first chamber (10, 20) define the first cavity (11, 12, 13). The first chamber (10, 20) includes a first cavity manifold 10 and a first exhaust manifold 20. The first cavity manifold 10 defines all side surfaces of the first cavity (11, 12, 13), and the first exhaust manifold 20 defines an end surface of the first cavity (11, 12, 13), which is the end surface of the first widening-taper conical cavity portion 13. The first cavity manifold 10 may include at least one empty volume 19 to reduce the weight of the first cavity manifold 10. In one embodiment, the at least one empty volume 19 may be topologically homeomorphic to a torus. As used here, being "topologically homeomorphic to an element" refers to having the feature of topological homeomorphism to the element as known in mathematics.

At least one first corona wire 18 is disposed within the first cylindrical cavity portion 12. The at least one first corona wire 18 is a conductive wire that is employed to generate a corona. As used herein, a corona refers to an atmospheric environment including an electrical field having a magnitude is within a range of 0.1-0.999 times the breakdown field of the atmospheric environment. As used herein, an "atmospheric environment" refers to a gaseous environment in which the total pressure is in a range from 0.1 times 101325 Pa (standard atmospheric pressure) to 3 times 101325 Pa, and includes any environment within the troposphere of the earth. As used herein, a "corona wire" refers to a conductive wire composed of a conductive material and capable of generating a corona. Each of the at least one first corona wire 18 can be a conductive metallic wire of a uniform cross-sectional area that is invariant under translation along the lengthwise direction of the first corona wire 18. Within the corona, a faint glow can envelop the at least one first corona wire 18, and streamers directed toward electrically grounded structures may be generated. While the present invention is described employing an embodiment in which a single first corona wire 18 is employed, embodiments are expressly contemplated in which a plurality of first corona wires 18 are employed.

The first narrowing-taper conical cavity portion 11 has an increasing horizontal cross-sectional area that increases with distance from the at least one first corona wire 18. The first widening-taper conical cavity portion 13 has an increasing horizontal cross-sectional area that increases with distance from the at least one first corona wire 18.

At least one first grounded sample collection plate 24 is located on a wall of the first cavity (11, 12, 13). The at least one first grounded sample collection plate 24 can be located at a base of the first widening-taper conical cavity portion 13. In one embodiment, the at least one first grounded sample collection plate 24 can be located at a center region of the base of the first widening-taper conical cavity portion 13.

The at least one first grounded sample collection plate 24 is disposed downstream of the at least one first corona wire 18. In one embodiment, the at least one grounded sample collection plate 24 can be disposed downstream of the entirety of the at least one first corona wire 18. The corona within the first cavity (11, 12, 13) is present between the at least one first corona wire 18 and the at least one first grounded sample collection plate 24.

Each of the at least one first grounded sample collection plate 24 can be electrically grounded by a series of conductive elements (26, 28). The series of conductive elements (26, 28) can include, for example, a first grounding stud 26 and a first grounding tether 28.

The at least one first corona wire 18 can be electrically biased with a positive voltage or with a negative voltage. The electrical bias voltage can be provided by a high voltage application circuitry configured to generate a corona between the at least one first corona wire 18 and the at least one first grounded sample collection plate 24. The high voltage application circuitry can be any direct current (DC) voltage application circuitry known in the art provided that the voltage supplied is high enough voltage that generates a corona within the first cavity (11, 12, 13). The first chamber (10, 20) includes a dielectric material that prevents electrical discharge of corona. In one embodiment, the first chamber (10, 20) can include a plastic material such as polycarbonate.

The first exemplary electrostatic aerosol sampling apparatus can include at least one means for inducing an air flow through the first cavity (11, 12, 13). The at least one means can be, for example, an engine (such as an engine of a drone) that can propel the first stage S1 and any attachments thereto in a manner that induces an air flow through the first cavity (11, 12, 13). Alternately or additionally, the at least one means can be, for example, a fan (not shown) configured to blow air into the first cavity (11, 12, 13).

The first narrowing-taper conical cavity portion 11 functions as an air inlet channel. A plurality of first holes 29 can be located within the first exhaust manifold 20 between the center region and the periphery of the base of the first widening-taper conical cavity portion 13. The plurality of first holes 29 within the first exhaust manifold 20 functions as an air outlet channel.

The first cylindrical cavity portion 12 does not overlap with the plurality of first holes 29 in a view along the axial direction of the first exemplary electrostatic aerosol sampling apparatus. The axial direction of the first exemplary electrostatic aerosol sampling apparatus is the direction of the axial symmetry of the first cylindrical cavity portion 12, which coincides with the reference direction, i.e., the direction of the air flow within the first cylindrical cavity portion 12.

In one embodiment, the direction of the air flow at each first corona wire 18 can be substantially perpendicular to the surface of the at least one first grounded sample collection plate 24 on which aerosols in the air flow impinge. As used herein, two elements are "substantially perpendicular" to each other if the angle between the two elements is between 85 degrees and 95 degrees. In one embodiment, the direction of the air flow at the at least one first corona wire 18 can be substantially perpendicular to the lengthwise direction of the at least one corona wire 18.

In one embodiment, the at least one first grounded sample collection plate 24 can be mounted on a wall of the first cavity (11, 12, 13). The wall can include a plurality of first holes 29 that allow passage of the air flow therethrough.

In one embodiment, the at least one first corona wire 18 intersects an axis of symmetry of the first cylindrical cavity 12 at a right angle. Except for the asymmetry introduced by the series of conductive elements (26, 28) to electrically ground the at least one first grounded sample collection plate 24 and the asymmetry introduced by the at least one first corona wire 18, the first stage S1 can have an axial symmetry around an axis passing through the center of the first cylindrical cavity portion 12 along the direction of the air flow.

The second stage S2 includes a second cavity (31, 32, 33). The second stage S2 can be structurally equivalent to the first stage S1, and can be adjoined to the exhaust side of the first stage S1 so that the air flow proceeds from the plurality of first holes 29 into the second cavity (31, 32, 33). In one embodiment, the second cavity (31, 32, 33) can include a second narrowing-taper conical cavity portion 31, a second cylindrical cavity portion 32 adjoining a narrow periphery of the narrowing-taper conical cavity portion 31, and a second widening-taper conical cavity portion 33 adjoining the second cylindrical cavity portion 32 at one end of the second cylindrical cavity portion 32. The reference direction in the second exemplary electrostatic aerosol sampling apparatus is the direction along which an air flow proceeds within the second cylindrical cavity portion 32.

Interior surfaces of a second chamber (30, 40) define the second cavity (31, 32, 33). The second chamber (30, 40) includes a second cavity manifold 30 and a second exhaust manifold 40. The second cavity manifold 30 defines all side surfaces of the second cavity (31, 32, 33), and the second exhaust manifold 40 defines an end surface of the second cavity (31, 32, 33), which is the end surface of the second widening-taper conical cavity portion 33. The second cavity manifold 30 may include at least one empty volume 39 to reduce the weight of the second cavity manifold 30. In one embodiment, the at least one empty volume 39 may be topologically homeomorphic to a torus.

At least one second corona wire 38 is disposed within the second cylindrical cavity portion 32. The at least one second corona wire 38 is a conductive wire that is employed to generate a corona. Each of the at least one second corona wire 38 can be a conductive metallic wire of a uniform cross-sectional area that is invariant under translation along the lengthwise direction of the second corona wire 38. Within the corona, a faint glow can envelop the at least one second corona wire 38, and streamers directed toward electrically grounded structures may be generated. While the present invention is described employing an embodiment in which a single second corona wire 38 is employed, embodiments are expressly contemplated in which a plurality of second corona wires 38 are employed.

The second narrowing-taper conical cavity portion 31 has an increasing horizontal cross-sectional area that increases with distance from the at least one second corona wire 38. The second widening-taper conical cavity portion 33 has an increasing horizontal cross-sectional area that increases with distance from the at least one second corona wire 38.

At least one second grounded sample collection plate 44 is located on a wall of the cavity (31, 32, 33). The at least one second grounded sample collection plate 44 can be located at a base of the second widening-taper conical cavity portion 33. In one embodiment, the at least one second grounded sample collection plate 44 can be located at a center region of the base of the second widening-taper conical cavity portion 33.

The at least one second grounded sample collection plate 44 is disposed downstream of the at least one second corona wire 38. In one embodiment, the at least one grounded sample collection plate 44 can be disposed downstream of the entirety of the at least one second corona wire 38. The corona within the second cavity (31, 32, 33) is present between the at least one second corona wire 38 and the at least one second grounded sample collection plate 44.

Each of the at least one second grounded sample collection plate 44 can be electrically grounded by a series of conductive elements (46, 48). The series of conductive elements (46, 48) can include, for example, a second grounding stud 46 and a second grounding tether 48.

The at least one second corona wire 38 can be electrically biased with a positive voltage or with a negative voltage. The electrical bias voltage can be provided by a high voltage application circuitry configured to generate a corona between the at least one second corona wire 38 and the at least one second grounded sample collection plate 44. The high voltage application circuitry can be any direct current (DC) voltage application circuitry known in the art provided that the voltage supplied is high enough voltage that generates a corona within the second cavity (31, 32, 33). The second chamber (30, 40) includes a dielectric material that prevents electrical discharge of corona. In one embodiment, the second chamber (30, 40) can include a plastic material such as polycarbonate.

The second narrowing-taper conical cavity portion 31 functions as an air inlet channel. A plurality of second holes 49 can be located within the second exhaust manifold 40 between the center region and the periphery of the base of the second widening-taper conical cavity portion 33. The plurality of second holes 49 within the second exhaust manifold 40 functions as an air outlet channel.

The second cylindrical cavity portion 32 does not overlap with the plurality of second holes 49 in a view along the axial direction of the second exemplary electrostatic aerosol sampling apparatus. The axial direction of the second exemplary electrostatic aerosol sampling apparatus is the direction of the axial symmetry of the second cylindrical cavity portion 32, which coincides with the reference direction, i.e., the direction of the air flow within the second cylindrical cavity portion 32.

In one embodiment, the direction of the air flow at each second corona wire 38 can be substantially perpendicular to the surface of the at least one second grounded sample collection plate 44 on which aerosols in the air flow impinge. In one embodiment, the direction of the air flow at the at least one second corona wire 38 can be substantially perpendicular to the lengthwise direction of the at least one corona wire 38.

In one embodiment, the at least one second grounded sample collection plate 44 can be mounted on a wall of the second cavity (31, 32, 33). The wall can include a plurality of second holes 49 that allow passage of the air flow therethrough.

In one embodiment, the at least one second corona wire 38 intersects an axis of symmetry of the second cylindrical cavity 32 at a right angle. Except for the asymmetry introduced by the series of conductive elements (46, 48) to electrically ground the at least one second grounded sample collection plate 44 and the asymmetry introduced by the at least one second corona wire 38, the second stage S1 can have an axial symmetry around an axis passing through the center of the second cylindrical cavity portion 32 along the direction of the air flow.

A support structure 50 may be optionally added to the exhaust of the second stage S2. A cavity 51 within the support structure 50 can be connected to the plurality of second holes 49 within the second exhaust manifold 40. At least one additional stage (not shown) that is structurally equivalent to the first stage S1 or the second stage S2 can be optionally added between the second stage S2 and the support structure. Alternately, the first exemplary electrostatic aerosol sampling apparatus can be operated only within the first stage S1.

The first exemplary electrostatic aerosol sampling apparatus can be employed to generate a plurality of aerosol samples. Accumulation of an aerosol material can be induced on the at least one grounded sample collection plate (24, 44) by causing air to pass through the cavities (11, 12, 13, 31, 32, 33). At least one means for inducing the air flow can be employed, while a corona is present between the at least one corona wire (18, 38) and each of the at least one grounded sample collection plate (24, 44) within each of the first chamber (10, 20) and the second chamber (30, 40).

The at least one grounded sample collection plate (24, 44) can be a plurality of grounded sample collection plates (24, 44). A plurality of aerosol samples can be collected, which include different materials caused by different degrees of ionization of materials in the air flow.

Figure 2A:
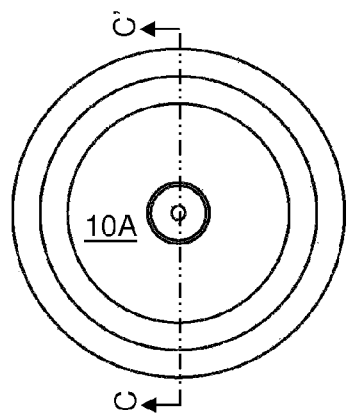
FIG. 2A is another top-down view of the first exemplary electrostatic aerosol sampling apparatus according to the first embodiment of the present disclosure.
Figure 2B:
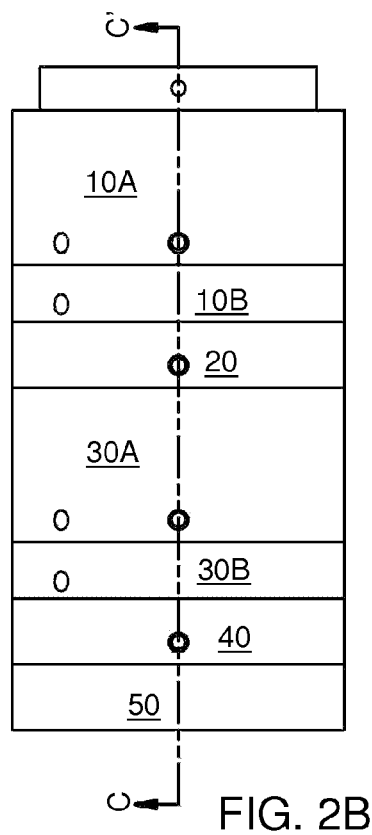
FIG. 2B is a side view of the first exemplary electrostatic aerosol sampling apparatus of FIG. 2A.
Figure 2C:
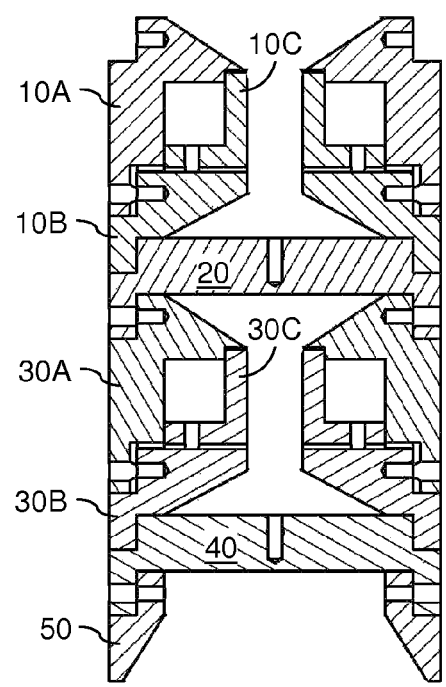
FIG. 2C is a cross-sectional view of the first exemplary electrostatic aerosol sampling apparatus along the plane C-C' of FIGS. 2A and 2B.

Referring to FIGS. 2A-2C, the first exemplary electrostatic aerosol sampling apparatus is shown without any grounded sample collection plate or any conductive structures for electrically grounding the grounded sample collection plate. The first cavity manifold (10A, 10B, 10C) can include discrete parts that can be assembled to define the first cavity (11, 12, 13). For example, the first cavity manifold (10A, 10B, 10C) can include a first front cavity manifold 10A, a first rear cavity manifold 10B, and a first inner cavity manifold 10C. The second cavity manifold (30A, 30B, 30C) can include discrete parts that can be assembled to define the second cavity (31, 32, 33). For example, the second cavity manifold (30A, 30B, 30C) can include a second front cavity manifold 30A, a second rear cavity manifold 30B, and a second inner cavity manifold 30C.

Figure 3:
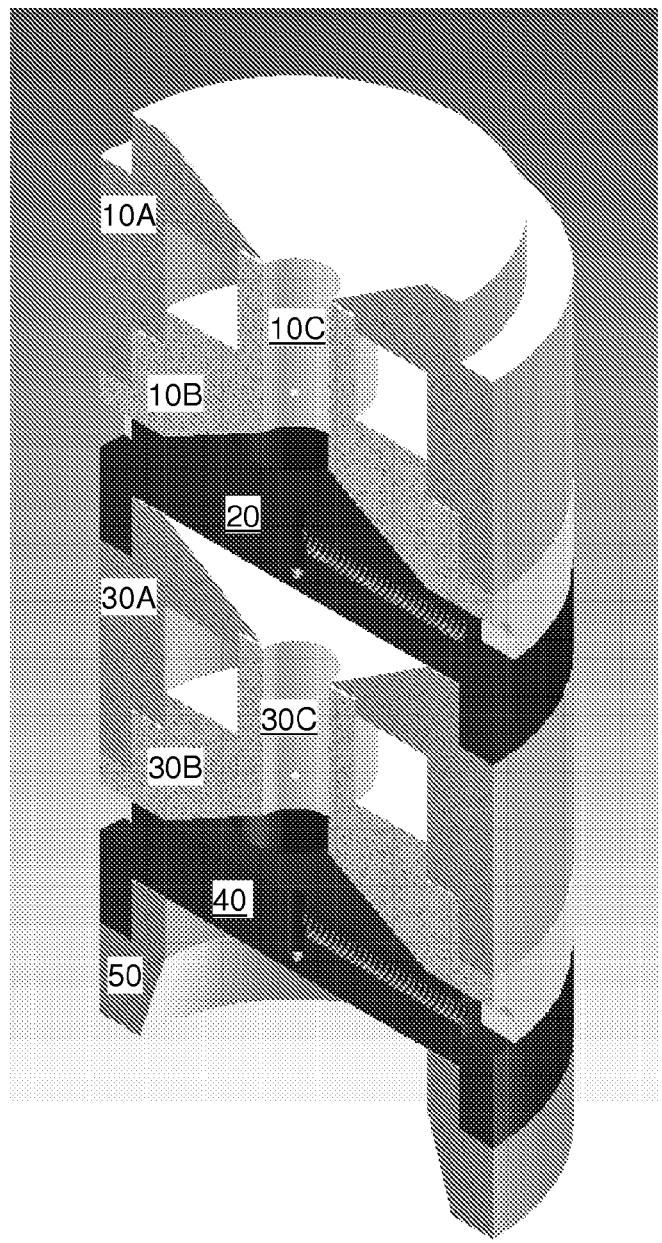
FIG. 3 is a schematic bird's eye view of one half of the first exemplary electrostatic aerosol sampling apparatus of FIGS. 2A-2C.

FIG. 3 shows various views of the first exemplary electrostatic aerosol sampling apparatus according to the present disclosure.

Figure 4:
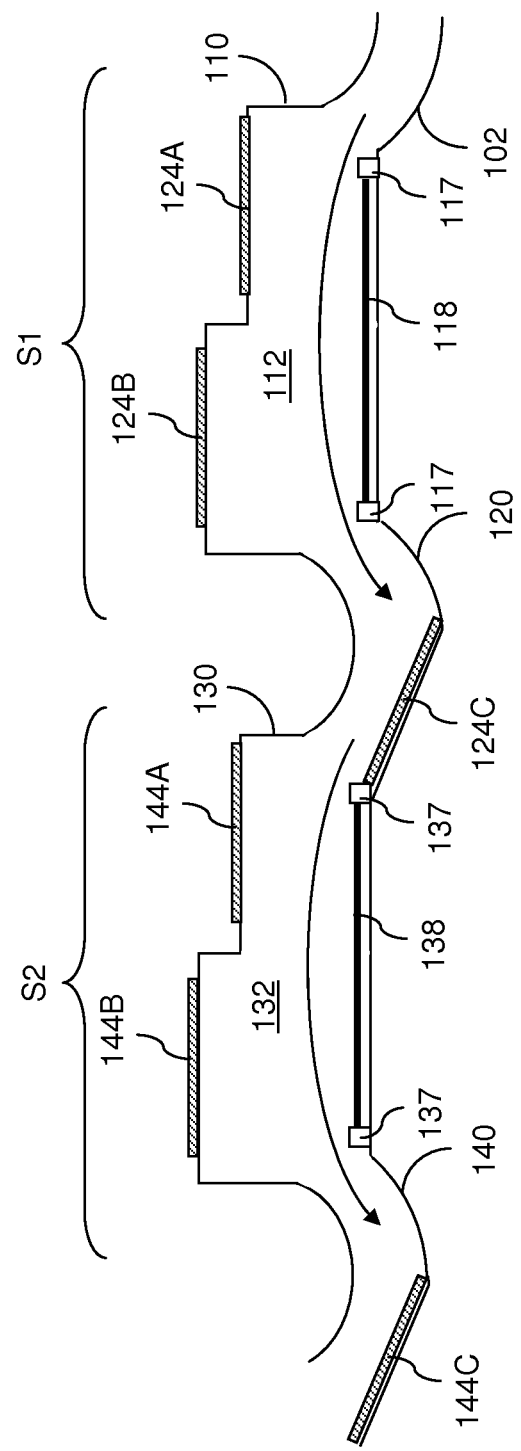
FIG. 4 is a vertical cross-sectional view of a second exemplary electrostatic aerosol sampling apparatus according to a second embodiment of the present disclosure.

Referring to FIG. 4, a second exemplary electrostatic aerosol sampling apparatus according to a second embodiment of the present disclosure is illustrated. The second exemplary electrostatic aerosol sampling apparatus includes a first stage S1 and a second stage S2 that are adjoined to each other such that air flow exiting the first stage S1 enters the second stage S2.

The first stage S1 includes a first cavity 112, which is configured to allow an air flow therethrough. A first air inlet channel 102 is attached to the inlet side of the first cavity 112, and a first air outlet channel 120 is attached to the outlet side of the first cavity 112. The reference direction in the second exemplary electrostatic aerosol sampling apparatus is the direction along which an air flow proceeds within the first cavity 112.

Interior surfaces of a first chamber 110 define the first cavity 112. At least one first corona wire 118 is disposed within the first cavity 112. The at least one first corona wire 118 is a conductive wire that is employed to generate a corona. Each of the at least one first corona wire 118 can be a conductive metallic wire of a uniform cross-sectional area that is invariant under translation along the lengthwise direction of the first corona wire 118. Within the corona, a faint glow can envelop the at least one first corona wire 118, and streamers directed toward electrically grounded structures may be generated. While the present invention is described employing an embodiment in which a single first corona wire 118 is employed, embodiments are expressly contemplated in which a plurality of first corona wires 118 are employed.

At least one first grounded sample collection plate (124A, 124B, 124C) can be located on a wall of the first cavity 112. The at least one first grounded sample collection plate 24 can be located at portions of the first cavity 112 that face the at least one first corona wire 118. In one embodiment, the at least one first grounded sample collection plate (124A, 124B, 124C) can be a plurality of first grounded sample collection plates (124A, 124B, 124C). For example, a grounded sample collection plate (which is herein referred to as a first front-side grounded sample collection plate 124A) can be located on a first portion of a wall of the first cavity 112, and another grounded sample collection plate (which is herein referred to as a first rear-side grounded sample collection plate 124B) can be located on a second portion of the wall of the first cavity 112 and downstream of the first front-side grounded sample collection plate 124A.

In one embodiment, the second portion of the wall, on which the first rear-side grounded sample collection plate 124B is mounted, can be recessed farther away from the at least one first corona wire 118 than the first portion, on which the first front-side grounded sample collection plate 124B) is mounted, is from the at least one first corona wire 118. In one embodiment, the at least one first corona wire 118 is parallel to the first front-side grounded sample collection plate 124A and the first rear-side grounded sample collection plate 124B. The recessing of the first rear-side grounded sample collection plate 124B relative to the first front-side grounded sample collection plate 124A can change the distribution of particle sizes within the collected aerosol. In some instances, the recessing of the first rear-side grounded sample collection plate 124B relative to the first front-side grounded sample collection plate 124A may change the ratio of ionized materials to non-ionized materials in the aerosol sample deposited on the first rear-side grounded sample collection plate 124B.

At least one portion of the at least one first grounded sample collection plate (124A, 124B, 124C) can be disposed downstream of the at least one first corona wire 118. In one embodiment, a portion of one of the at least one first grounded sample collection plate (124A, 124B, 124C) can be disposed upstream of the at least one corona wire 118. For example, an edge of the first front-side grounded sample collection plate 124A can be located upstream of the at least one first corona wire 118. The corona within the first cavity 112 is present between the at least one first corona wire 118 and the at least one first grounded sample collection plate (124A, 124B, 124C).

The at least one first corona wire 118 can be electrically biased with a positive voltage or with a negative voltage. The electrical bias voltage can be provided by a high voltage application circuitry configured to generate a corona between the at least one first corona wire 118 and the at least one first grounded sample collection plate (124A, 124B, 124C). The high voltage application circuitry can be any direct current (DC) voltage application circuitry known in the art, provided that the voltage supplied is high enough voltage that generates a corona within the first cavity 112. The first chamber 110 includes a dielectric material that prevents electrical discharge of corona. In one embodiment, the first chamber 110 can include a plastic material such as polycarbonate.

The second exemplary electrostatic aerosol sampling apparatus can include at least one means for inducing an air flow through the first cavity 112. The at least one means can be, for example, an engine (such as an engine of a drone) that can propel the first stage S1 and any attachments thereto in a manner that induces an air flow through the first cavity 112. Alternately or additionally, the at least one means can be, for example, a fan (not shown) configured to blow air into the first cavity 112.

In one embodiment, the direction of the air flow at each first corona wire 118 can be substantially parallel to the surface of the at least one first grounded sample collection plate (124A, 124B, 124C) on which aerosols in the air flow impinge. As used herein, two elements are "substantially parallel" to each other if the angle between the two elements is less than 5 degrees. In one embodiment, the direction of the air flow at the at least one first corona wire 118 can be substantially parallel to the lengthwise direction of the at least one corona wire 118.

In one embodiment, the at least one first grounded sample collection plate (124A, 124B, 124C) can optionally include an exhaust-side grounded sample collection plate 124C, which can be mounted within the first air outlet channel 120. The exhaust-side grounded sample collection plate 124C can be mounted where the direction of air flow changes within the first air outlet channel 120.

The second stage S2 includes a second cavity 132. The second stage S2 can be structurally equivalent to the first stage S1, and can be adjoined to the exhaust side of the first stage S1 so that the air flow proceeds from first cavity 112 into the second cavity 132 through the first air outlet channel 120.

The second stage S2 includes a second cavity 132, which is configured to allow an air flow therethrough. The first air outlet channel 120 is attached to the inlet side of the second cavity 132, and a second air outlet channel 140 is attached to the outlet side of the second cavity 132. The reference direction in the second exemplary electrostatic aerosol sampling apparatus is the direction along which an air flow proceeds within the second cavity 132.

Interior surfaces of a second chamber 130 define the second cavity 132. At least one second corona wire 138 is disposed within the second cavity 132. The at least one second corona wire 138 is a conductive wire that is employed to generate a corona. Each of the at least one second corona wire 138 can be a conductive metallic wire of a uniform cross-sectional area that is invariant under translation along the lengthwise direction of the second corona wire 138. Within the corona, a faint glow can envelop the at least one second corona wire 138, and streamers directed toward electrically grounded structures may be generated. While the present invention is described employing an embodiment in which a single second corona wire 138 is employed, embodiments are expressly contemplated in which a plurality of second corona wires 138 are employed.

At least one second grounded sample collection plate (144A, 144B, 144C) can be located on a wall of the second cavity 132. The at least one second grounded sample collection plate 24 can be located at portions of the second cavity 132 that face the at least one second corona wire 138. In one embodiment, the at least one second grounded sample collection plate (144A, 144B, 144C) can be a plurality of second grounded sample collection plates (144A, 144B, 144C). For example, a grounded sample collection plate (which is herein referred to as a second front-side grounded sample collection plate 144A) can be located on a second portion of a wall of the second cavity 132, and another grounded sample collection plate (which is herein referred to as a second rear-side grounded sample collection plate 144B) can be located on a second portion of the wall of the second cavity 132 and downstream of the second front-side grounded sample collection plate 144A.

In one embodiment, the second portion of the wall, on which the second rear-side grounded sample collection plate 144B is mounted, can be recessed farther away from the at least one second corona wire 138 than the second portion, on which the second front-side grounded sample collection plate 144B) is mounted, is from the at least one second corona wire 138. In one embodiment, the at least one second corona wire 138 is parallel to the second front-side grounded sample collection plate 144A and the second rear-side grounded sample collection plate 144B. The recessing of the second rear-side grounded sample collection plate 144B relative to the second front-side grounded sample collection plate 144A can change the distribution of particle sizes within the collected aerosol. In some instances, the recessing of the second rear-side grounded sample collection plate 144B relative to the second front-side grounded sample collection plate 144A may change the ratio of ionized materials to non-ionized materials in the aerosol sample deposited on the second rear-side grounded sample collection plate 144B.

At least one portion of the at least one second grounded sample collection plate (144A, 144B, 144C) can be disposed downstream of the at least one second corona wire 138. In one embodiment, a portion of one of the at least one second grounded sample collection plate (144A, 144B, 144C) can be disposed upstream of the at least one corona wire 138. For example, an edge of the second front-side grounded sample collection plate 144A can be located upstream of the at least one second corona wire 138. The corona within the second cavity 132 is present between the at least one second corona wire 138 and the at least one second grounded sample collection plate (144A, 144B, 144C).

The at least one second corona wire 138 can be electrically biased with a positive voltage or with a negative voltage. The electrical bias voltage can be provided by a high voltage application circuitry configured to generate a corona between the at least one second corona wire 138 and the at least one second grounded sample collection plate (144A, 144B, 144C). The high voltage application circuitry can be any direct current (DC) voltage application circuitry known in the art, provided that the voltage supplied is high enough voltage that generates a corona within the second cavity 132. The second chamber 130 includes a dielectric material that prevents electrical discharge of corona. In one embodiment, the second chamber 130 can include a plastic material such as polycarbonate.

In one embodiment, the direction of the air flow at each second corona wire 138 can be substantially parallel to the surface of the at least one second grounded sample collection plate (144A, 144B, 144C) on which aerosols in the air flow impinge. As used herein, two elements are "substantially parallel" to each other if the angle between the two elements is less than 5 degrees. In one embodiment, the direction of the air flow at the at least one second corona wire 138 can be substantially parallel to the lengthwise direction of the at least one corona wire 138.

In one embodiment, the at least one second grounded sample collection plate (144A, 144B, 144C) can optionally include an exhaust-side grounded sample collection plate 144C, which can be mounted within the second air outlet channel 140. The exhaust-side grounded sample collection plate 144C can be mounted where the direction of air flow changes within the second air outlet channel 140.

At least one additional stage (not shown) that is structurally equivalent to the first stage S1 or the second stage S2 can be optionally added to the exhaust side of the second stage S2. Alternately, the second exemplary electrostatic aerosol sampling apparatus can be operated only within the first stage S1.

The second exemplary electrostatic aerosol sampling apparatus can be employed to generate a plurality of aerosol samples. Accumulation of an aerosol material can be induced on the at least one grounded sample collection plate (124A, 124B, 124C, 144A, 144B, 144C) by causing air to pass through the cavities (112, 132). At least one means for inducing the air flow can be employed, while a corona is present between the at least one corona wire (118, 138) and each of the at least one grounded sample collection plate (124A, 124B, 124C, 144A, 144B, 144C) within each of the first chamber 110 and the second chamber 130.

The at least one grounded sample collection plate (124A, 124B, 124C, 144A, 144B, 144C) can be a plurality of grounded sample collection plates (124A, 124B, 124C, 144A, 144B, 144C). A plurality of aerosol samples can be collected, which include different materials caused by different degrees of ionization of materials in the air flow.

Figure 5:
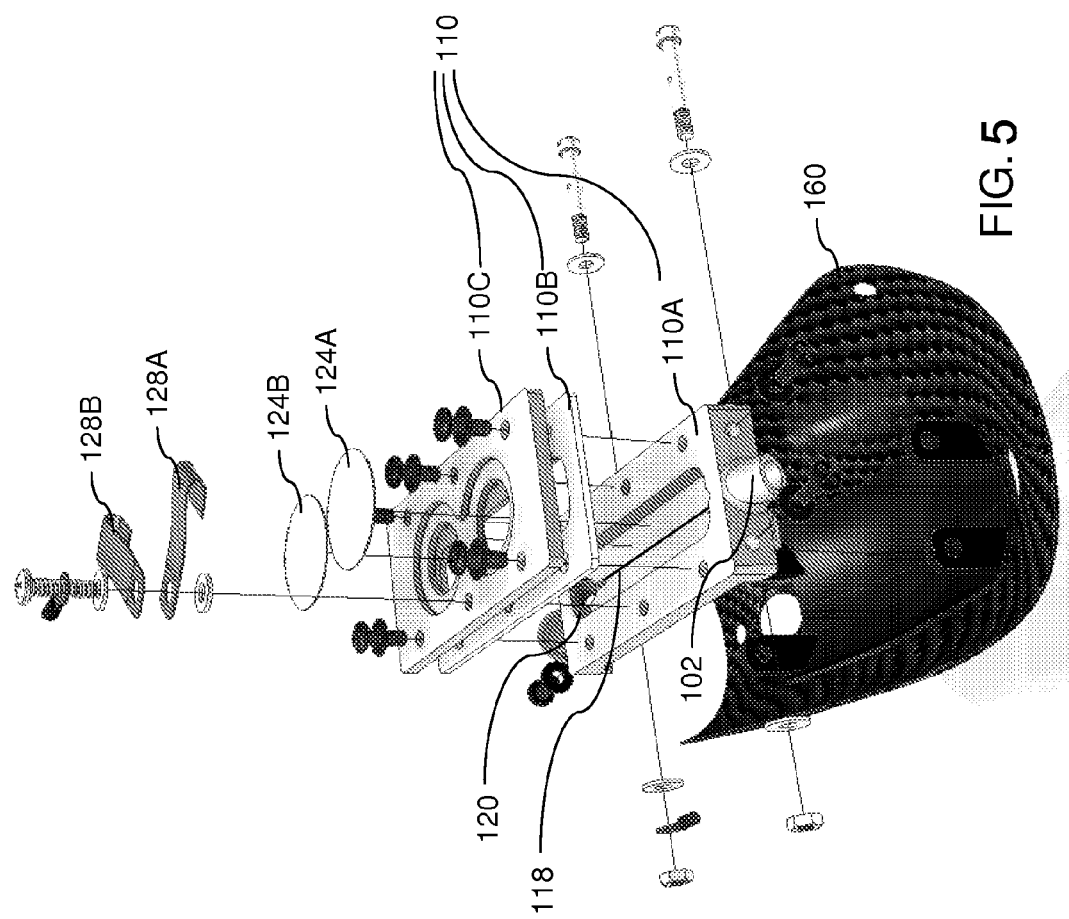
FIG. 5 is an exploded view of a sample of the second exemplary electrostatic aerosol sampling apparatus according to the second embodiment of the present disclosure.

FIG. 5 illustrates a design for the first stage S1 of the second exemplary electrostatic aerosol sampling apparatus in an exploded view. The first chamber 110 can be implements employing a set of discrete components, which can include a lower first chamber manifold 110A, a gasket 110B, and an upper first chamber manifold 110C. Further, conductive elements (128A, 128B) can be employed to electrically ground various grounded sample collection plates (124A, 124B). Various mechanical elements can be employed to provide physical integrity of the first stage S1. A protective cover element 160 can be employed to mount the first stage S1 and any additional stage (such as the second stage S2 illustrated in FIG. 4) to a platform, which can be a movable platform such as a drone.

FIG. 6 illustrates various views of the first stage S1 as mounted on the protective cover element 160 or standing alone at various angles.

Figure 7:
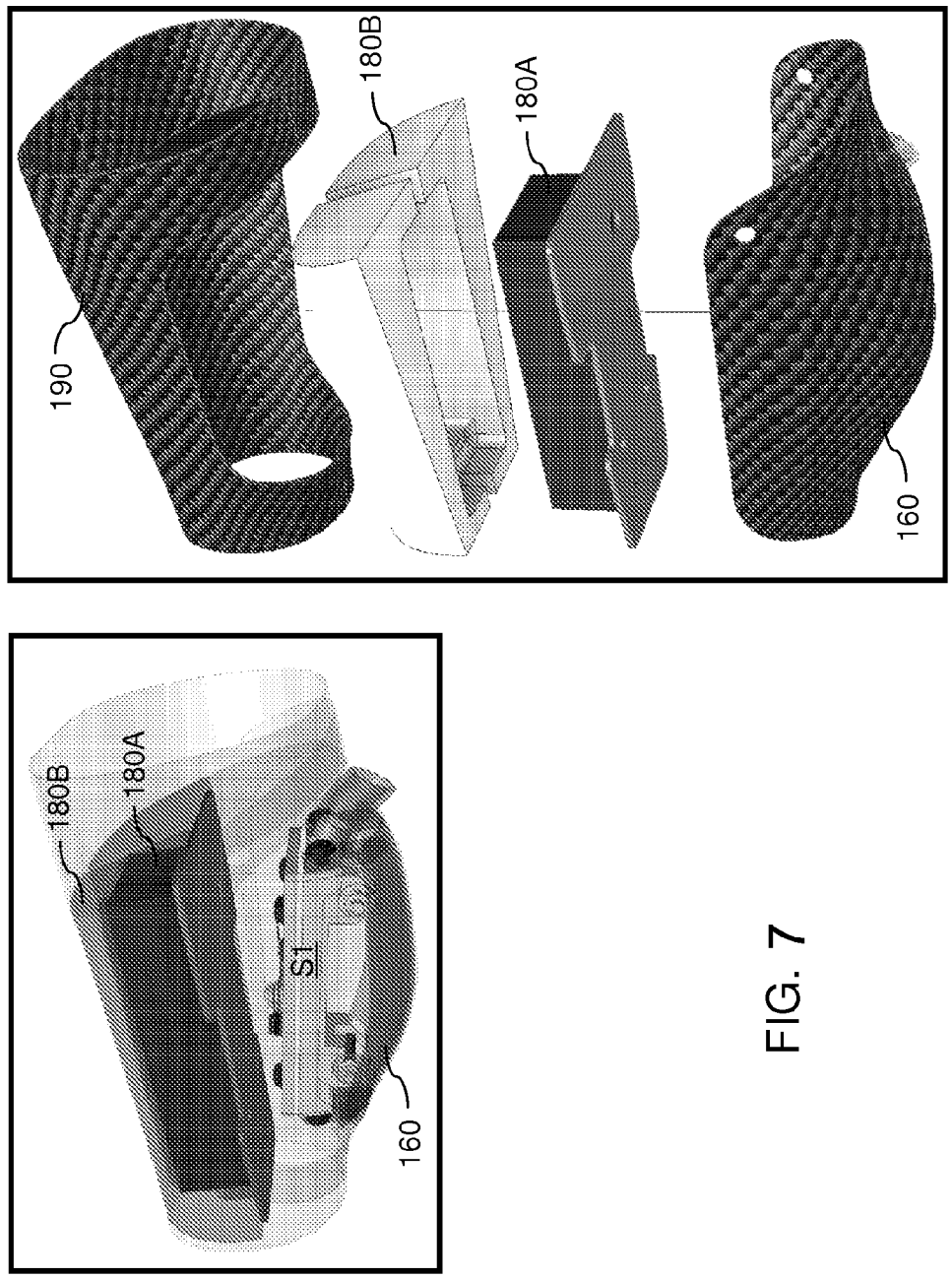
FIG. 7 shows a structure incorporating the second exemplary electrostatic aerosol sampling apparatus according to the second embodiment of the present disclosure.

FIG. 7 shows an assembly view and an exploded view of a structure incorporating the second exemplary electrostatic aerosol sampling apparatus. The structure can include the first stage S1, the protective cover element 160, a high voltage supply system 180A, an insulator structure 180B, and an upper casing element 190.

Figure 8:
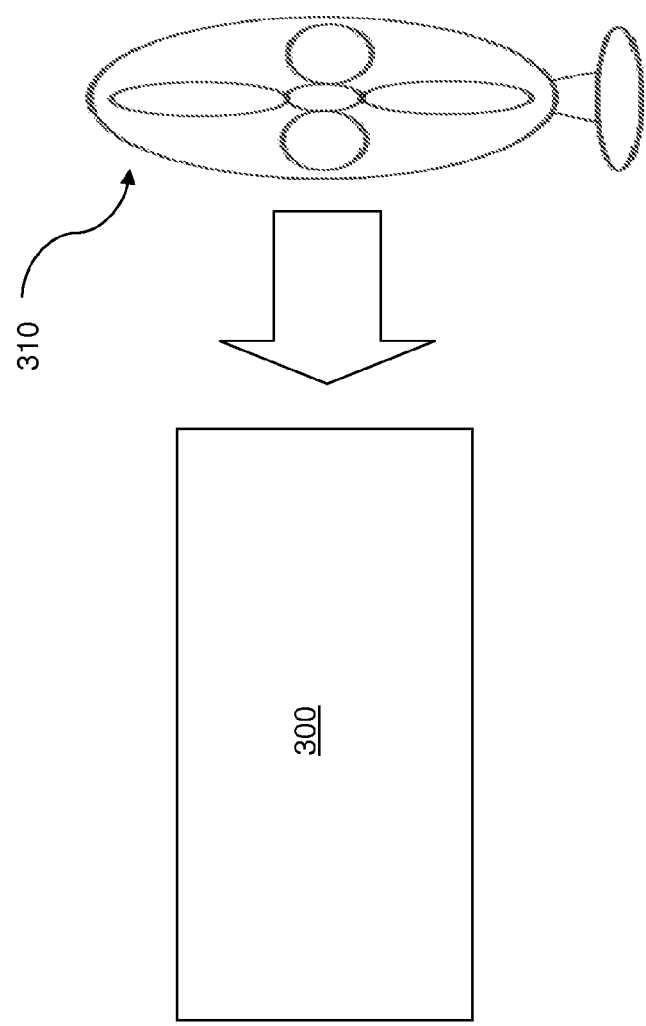
FIG. 8 illustrates a system including a fan configured to generate an air flow toward an exemplary electrostatic aerosol sampling apparatus according to the present disclosure.
Figure 10:
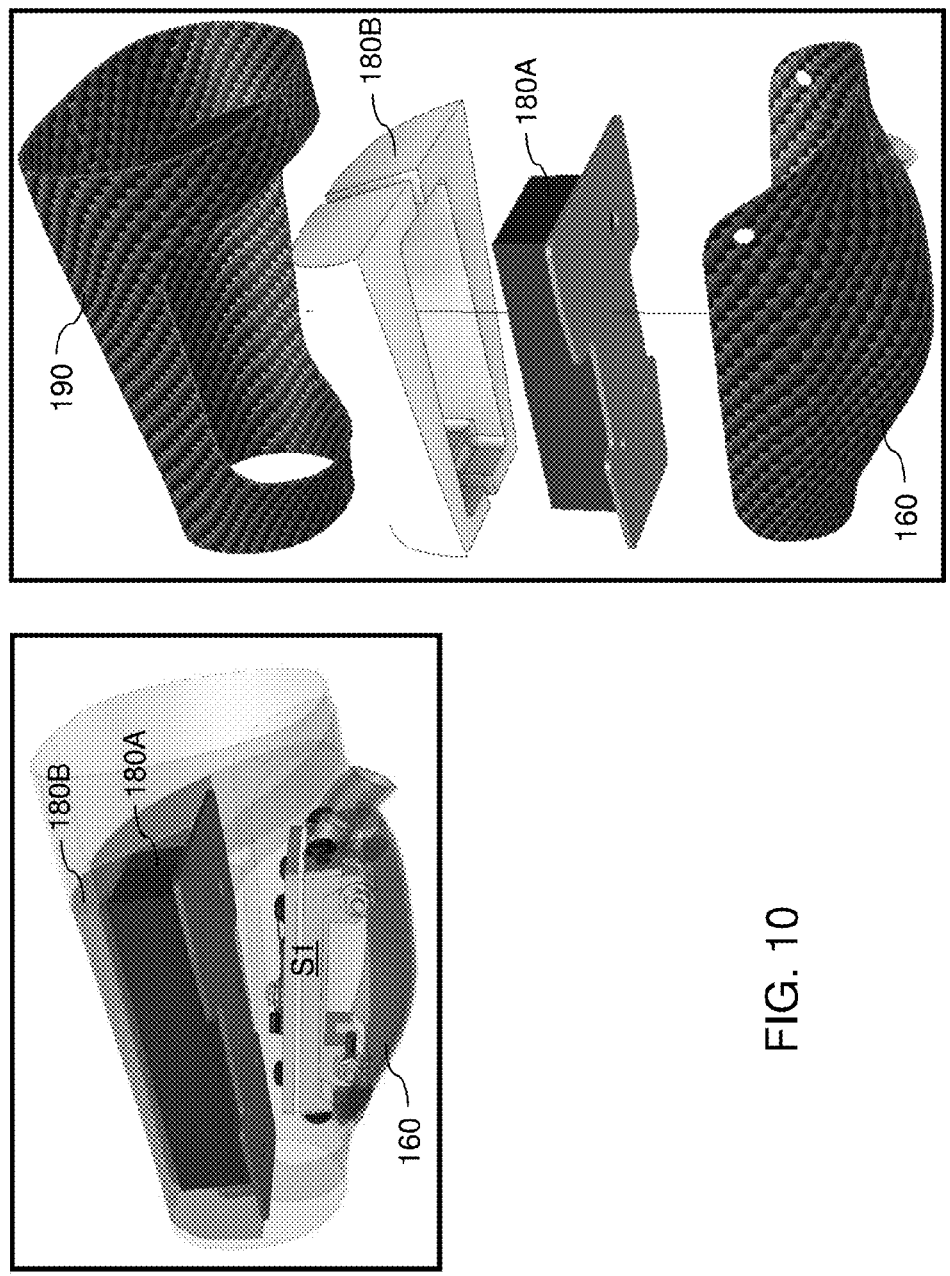
Figure 11:
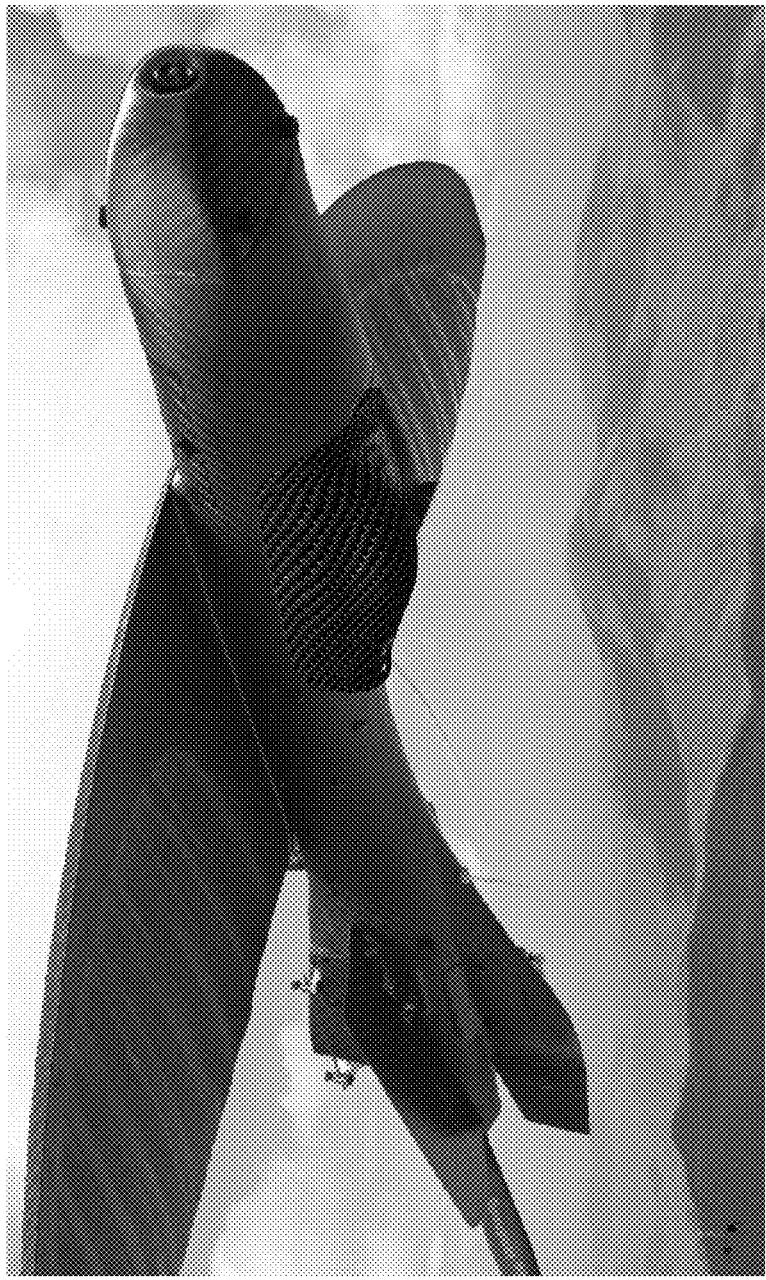
Figure 12:
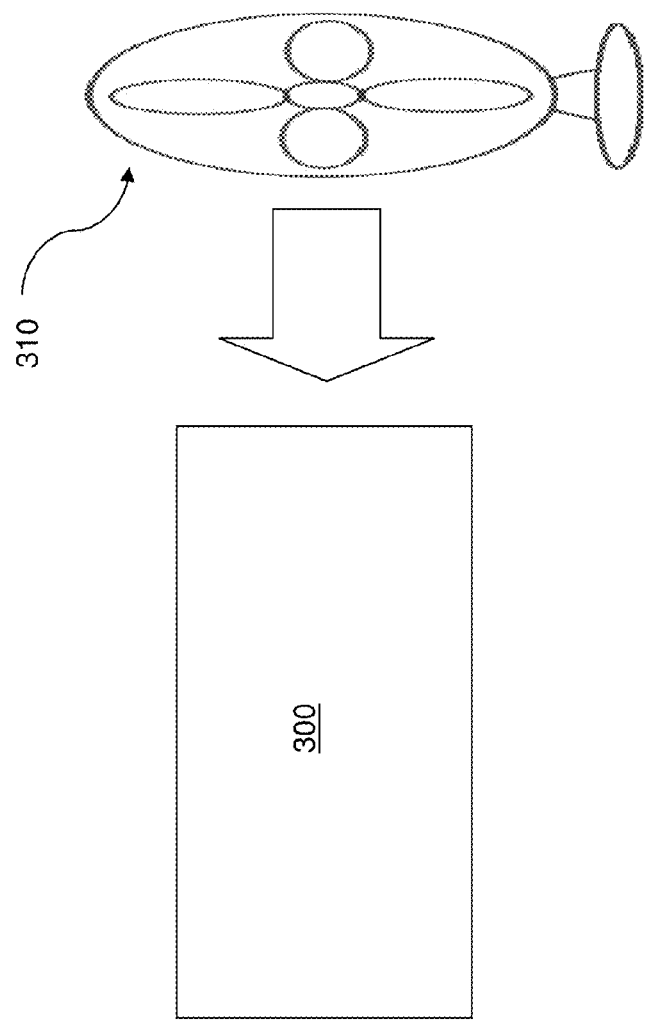

FIG. 8 illustrates a system including a fan 310 configured to generate an air flow toward an electrostatic aerosol sampling apparatus 300, which can be any of the exemplary electrostatic aerosol sampling apparatuses of the present disclosure.

The first exemplary electrostatic aerosol sampling apparatus can function as an impaction collection that collects aerosol samples for analysis. The various grounded sample collection plates can be analysis substrates that can be detached from the exemplary electrostatic aerosol sampling apparatuses of the present disclosure, and mounted directly as a sample in an analytic tool. The direct mounting of the analysis substrates minimizes the handling of the analysis substrates to reduce any chance of cross-contamination.

The present invention includes a versatile, specially designed electrostatic aerosol sampling apparatus. There are many benefits to the designs of the electrostatic aerosol sampling apparatuses over conventional electrostatic systems. In particular, the flow path is such that mounting of multiple stages is possible. Many stages can be present within the electrostatic aerosol sampling apparatuses of the present disclosure to allow for particle size separation. The grounded sample collection plates, i.e., the analysis substrates, are also constructed such that the grounded sample collection plates can be handled with a mechanical apparatus. Thus, the operator does not need to touch the grounded sample collection plates of the present disclosure with their hands, which greatly reducing the probability of cross contamination. For example, the grounded sample collection plates can be directly mounted into a scanning electron microscope (SEM), a secondary ion mass spectrometer (SIMS), an Auger spectrometer, or other analytical tools a for immediate analysis, further reducing manual sample manipulation.

The exemplary electrostatic aerosol sampling apparatuses of the present disclosure can be mounted on an unmanned aerial vehicle (UAV), i.e., a drone, for aerosol sampling of sundry analytes that may be present in the atmosphere, such as a plume from a vent stack, fire, or chemical or biological release. The exemplary electrostatic aerosol sampling apparatuses of the present disclosure can function as a unique platform that is mountable in a micro UAV for collecting air and/or aerosol samples. The present invention enhances the ability to collect such samples, and enables collection of samples that have heretofore been difficult or impossible to obtain.

The size of the exemplary electrostatic aerosol sampling apparatuses can vary depending on needs. The size of the grounded sample collection plates can be tailored so as to be mountable to analytical devices. The shape of the grounded sample collection plates can be selected to be conducive to analysis. In one embodiment, the grounded sample collection plates of the present disclosure can be small and easily accessible and/or observable. In one embodiment, the grounded sample collection plates of the present disclosure can be planar platelets without curvature therein.

Negative or positive potential can be applied to the at least one corona wire of the present disclosure. Because the grounded sample collection plates are electrically grounded, only a single high voltage power supply is needed per stage. Further, multiple stages can share the same high voltage power supply. In this case, a single high voltage power supply can power all corona wires within the exemplary electrostatic aerosol sampling apparatus of the present disclosure.

It is noted herein that single stage electrostatic precipitator allows for charging and collection all at once. This prevents collection of material in a charging stage, which is usually not suitable for analysis. Use of the multiple stages within the exemplary electrostatic aerosol sampling apparatuses of the present disclosure allows size segregation of aerosol and highly efficient collection.

Flow path of the air can be parallel or perpendicular to the collection substrate. A flow path that is perpendicular to the at least one corona wire as in the first embodiment allows for the combination of an impactor and electrostatic precipitator. A flow path that is parallel to the at least one corona wire as in the second embodiment allows for the lowest resistance to the flow. The electrostatic aerosol sampling apparatuses of the present disclosure offer particle size segregation and the ability to include many more stages.

The air flow through the electrostatic aerosol sampling apparatuses can be provided by a fan or via a moving vehicle.

Each corona wire may be made up of a taught wire which runs parallel to the face of the collection surface. One corona wire may be used to cover multiple stages, or there may be at least one corona wire per stage.

Each corona wire acts to form the electric field that drives the aerosol particles into the collection surface, i.e., the grounded sample collection plates. The electric field is non-uniform within the corona and across each grounded sample collection plate. The non-uniform electrical field can be advantageously employed to focus aerosol material within the corona into a region of the grounded sample collection plate that is suitable for analysis, e.g., into a center region.

The grounded sample collection plates can be configured to enable removal with clean tools, and to prevent cross contamination. In one embodiment, the grounded sample collection plates can be removed, and can be placed directly into an analytical instrument with little or no sample preparation on the part of the user.

In one embodiment, the output current from the at least one corona wire can be monitored to determine if the collection efficiency is decreasing. As the aerosol sample material is collected on the grounded sample collection plates, the collected aerosol material begins to form a resistive layer on the grounded sample collection plates, thereby reducing the effectiveness of collection.

Collection of an aerosol material can be focused along a predetermined region within the grounded sample collection plates (on which analysis is to be subsequently performed) as opposed to collection over the entire surface of the grounded sample collection plates. Such a focus on the region to be analyzed can help with the analytical analysis to be performed after the sample collection is completed.

The electrostatic aerosol sampling apparatus of the present disclosure can be small enough to enable deployment by a single person, or for the electrostatic aerosol sampling apparatus to be carried on aerial platforms. To reduce weight and to simplify the design of the electrostatic aerosol sampling apparatus, polycarbonate may be used for the material of construction of the body of the chamber(s) of the electrostatic aerosol sampling apparatus of the present disclosure. In this case, the corona wires may be operated at the highest voltages possible that does not cause the breakdown of the corona through arcing. The use of polycarbonate reduces the chances of the voltage leaking through the material of the chamber to the grounded sample collection plates.

While the invention has been described in terms of specific embodiments, it is evident in view of the foregoing description that numerous alternatives, modifications and variations will be apparent to those skilled in the art. Each of the various embodiments of the present disclosure can be implemented alone, or in combination with any other embodiments of the present disclosure unless expressly disclosed otherwise or otherwise impossible as would be known to one of ordinary skill in the art. Accordingly, the invention is intended to encompass all such alternatives, modifications and variations which fall within the scope and spirit of the invention and the following claims.

What is claimed is:

1. An electrostatic aerosol sampling apparatus comprising:
   a chamber including a cavity configured to allow an air flow therethrough;
   at least one corona wire located within said cavity;
   at least one grounded sample collection plate disposed downstream of a portion of said at least one corona wire;
   a high voltage application circuitry configured to generate a corona between said at least one corona wire and said at least one grounded sample collection plate; and
   at least one means for inducing an air flow through said cavity; wherein said cavity includes:
   a cylindrical cavity portion in which said at least one corona wire is disposed; and
   a conical cavity portion adjoining said cylindrical cavity portion and having an increasing horizontal cross-sectional area that increases with distance from said at least one corona wire, wherein said at least one grounded sample collection plate is located on a wall of said cavity located at a base of said conical cavity.

2. The electrostatic aerosol sampling apparatus of claim 1, further comprising:
   another chamber including another cavity therein and cascaded to said chamber such that said air flow enters said another chamber after exiting said chamber;
   at least another corona wire located within said another cavity; and
   at least another grounded sample collection plate disposed downstream of a portion of said at least another corona wire.

3. The electrostatic aerosol sampling apparatus of claim 1, wherein said at least one grounded sample collection plate is downstream of an entirety of said at least one corona wire.

4. The electrostatic aerosol sampling apparatus of claim 1, wherein a direction of said air flow at said at least one corona wire is substantially perpendicular to a surface of said at least one grounded sample collection plate on which aerosols in said air flow impinge.

5. The electrostatic aerosol sampling apparatus of claim 1, wherein a direction of said air flow at said at least one corona wire is substantially perpendicular to a lengthwise direction of said at least one corona wire.

6. The electrostatic aerosol sampling apparatus of claim 1, wherein said at least one grounded sample collection plate is mounted on a wall of said cavity, wherein said wall includes a plurality of holes that allow passage of said air flow therethrough.

7. The electrostatic aerosol sampling apparatus of Claim 1, wherein said at least one grounded sample collection plate is located at a center region of said base of said conical cavity portion, and a plurality of holes is located between said center region and a periphery of said base of said conical cavity portion.

8. The electrostatic aerosol sampling apparatus of Claim 1, wherein said cavity further includes another conical cavity portion located upstream of said cylindrical cavity portion and having an increasing horizontal cross-sectional area that increases with distance from said at least one corona wire.

9. The electrostatic aerosol sampling apparatus of Claim 1, wherein said at least one corona wire intersects an axis of symmetry of said cylindrical cavity portion at a right angle.

10. The electrostatic aerosol sampling apparatus of claim 1, wherein a portion of said at least one grounded sample collection plate is upstream of said at least one corona wire.

11. The electrostatic aerosol sampling apparatus of claim 1, wherein a direction of said air flow at said at least one corona wire is substantially parallel to a lengthwise direction of said at least one corona wire.

12. The electrostatic aerosol sampling apparatus of claim 1, wherein said at least one grounded sample collection plate is a plurality of grounded sample collection plates that includes:
   a first grounded sample collection plate located on a first portion of a wall of said cavity; and
   a second grounded sample collection plate located on a second portion of said wall of said cavity and downstream of said first grounded sample collection plate.

13. The electrostatic aerosol sampling apparatus of claim 12, wherein said second portion is recessed farther away from said at least one corona wire than said first portion is from said at least one corona wire.

14. The electrostatic aerosol sampling apparatus of claim 13, wherein said at least one corona wire is parallel to said first and second grounded sample collection plates.

15. The electrostatic aerosol sampling apparatus of claim 1, wherein one of said at least one grounded sample collection plate is located within an air outlet channel attached to said cavity.

16. The electrostatic aerosol sampling apparatus of claim 1, wherein said at least one means for inducing said air flow comprises a drone or a fan.

17. A method of collecting at least one aerosol sample comprising:
   providing an electrostatic aerosol sampling apparatus comprising:
   a chamber including a cavity configured to allow an air flow therethrough
   at least one corona wire located within said cavity;
   a plurality of grounded sample collection plates disposed downstream of a portion of said at least one corona wire;
   a high voltage application circuitry configured to generate a corona between said at least one corona wire and said at least one grounded sample collection plate; and
   at least one means for inducing an air flow through said cavity; and
   inducing accumulation of an aerosol material on said at plurality of grounded sample collection plates by causing air to pass through said cavity employing said at least one means for inducing said air flow while a corona is present between said at least one corona wire and each of said at least one grounded sample collection plate, wherein said method further comprises collecting a plurality of aerosol samples including different materials caused by different degrees of ionization of materials in said air flow.

18. The method of claim 17, wherein said electrostatic aerosol sampling apparatus further comprises:
   another chamber including another cavity therein and cascaded to said chamber through an air outlet channel of said chamber;
   at least another corona wire located within said another cavity; and
   at least another grounded sample collection plate disposed downstream of a portion of said at least another corona wire,
   wherein said method further comprises collecting a plurality of aerosol samples in said chamber and in said another chamber.

19. The method of claim 17, wherein said cavity includes:
   a cylindrical cavity portion in which said at least one corona wire is disposed; and
   a conical cavity portion adjoining said cylindrical cavity portion and having an increasing horizontal cross-sectional area that increases with distance from said at least one corona wire, wherein said at least one grounded sample collection plate is located on a wall of said cavity located at a base of said conical cavity.

* * * * *